United States Patent
Kupfer et al.

Patent Number: 6,152,890
Date of Patent: Nov. 28, 2000

[54] METHOD AND DEVICE FOR THE RECORDING, PRESENTATION AND AUTOMATIC CLASSIFICATION OF BIOMECHANICAL LOAD VARIABLES MEASURED ON A FREELY MOVING TEST PERSON DURING A WORK SHIFT

[75] Inventors: Jürgen Kupfer, Berlin; Rolf-Peter Ellegast, Bonn; Dietmar Reinert, St. Augustin, all of Germany

[73] Assignee: Hauptverband der gewerblichen Berufsgenossenschaften e.V., Sankt Augustin, Germany

[21] Appl. No.: 09/183,097

[22] Filed: Oct. 30, 1998

[30] Foreign Application Priority Data

Oct. 30, 1997 [DE] Germany ............... 297 19 250

[51] Int. Cl.⁷ ...................................... A61B 5/00
[52] U.S. Cl. ............................................. 600/595
[58] Field of Search .................. 600/587, 592, 600/594, 595

[56] References Cited

U.S. PATENT DOCUMENTS

| | | |
|---|---|---|
| 4,665,928 | 5/1987 | Linial et al. |
| 4,774,679 | 9/1988 | Carlin |
| 5,012,810 | 5/1991 | Strand et al. |
| 5,186,062 | 2/1993 | Roost .................. 600/592 |
| 5,471,405 | 11/1995 | Marsh .................. 600/592 |

FOREIGN PATENT DOCUMENTS

| | | |
|---|---|---|
| 0494749 A1 | 7/1992 | European Pat. Off. |
| WO 81/01506 | 11/1981 | WIPO |
| WO 87/00026 | 1/1987 | WIPO |
| WO 89/01760 | 3/1989 | WIPO |
| WO 95/32666 | 12/1995 | WIPO |
| WO 98/03110 | 1/1998 | WIPO |

*Primary Examiner*—Max Hindenburg
*Attorney, Agent, or Firm*—Collard & Roe, P.C.

[57] ABSTRACT

A device and a method for the recording, presentation and automatic classification of biomechanical load variables measured on a freely moving test person during a work shift. The invention consists of a series of electronic sensors and a series of measuring and storage electronics for recording the movement of a person at a work site. The measuring and storage electronics include at least two sensors and at least one gyroscope. The method for recording a person at a work site includes measuring a set of body angles over a period of time, and measuring the ground reaction force in the region of the sole of a test person's foot. The next steps involve determining the threshold values for the identification of postures, and comparing of the threshold values determined with the measured body angles to identify motion patterns. Next, the expected total ground reaction force is calculated and then subtracted from the measured total ground reaction force measured to determine externally exerted forces. Next, the process involves identifying the motion patterns and the output of load profiles. After deriving these measurements, the process involves deriving the acceleration and velocity component of the measured body angles and transforming them into individual joint forces and joint moments while taking account of the measured ground reaction force. The final step includes deriving a disc comparison force and presenting the time characteristic of the disk compression force as a load indication.

20 Claims, 14 Drawing Sheets

Fig. 7
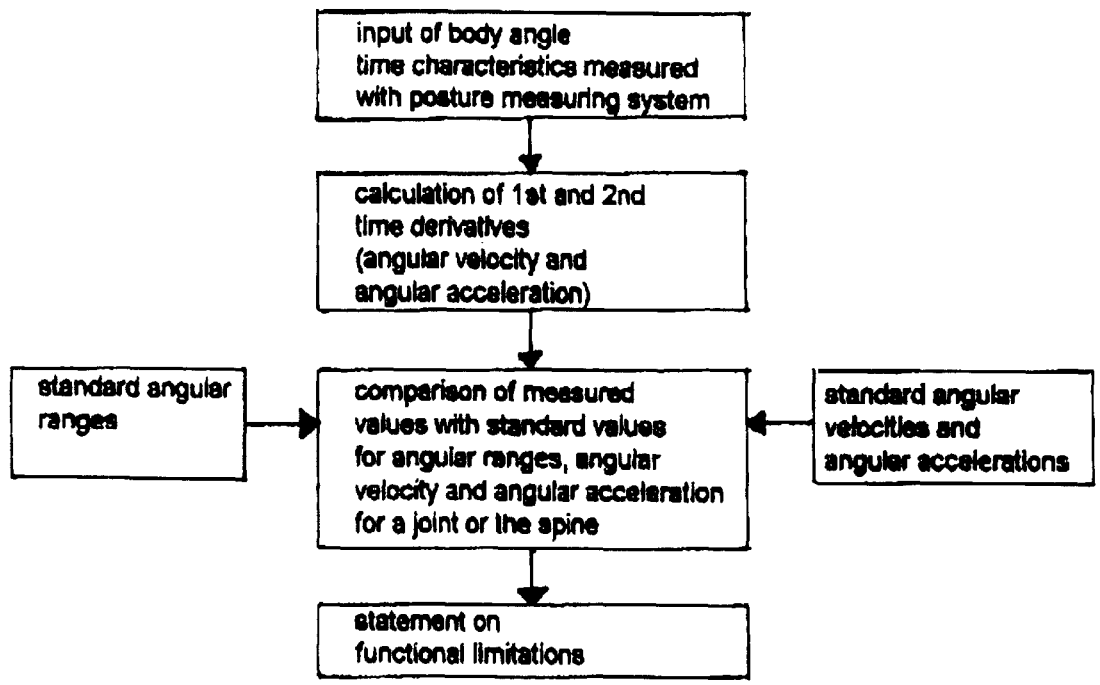
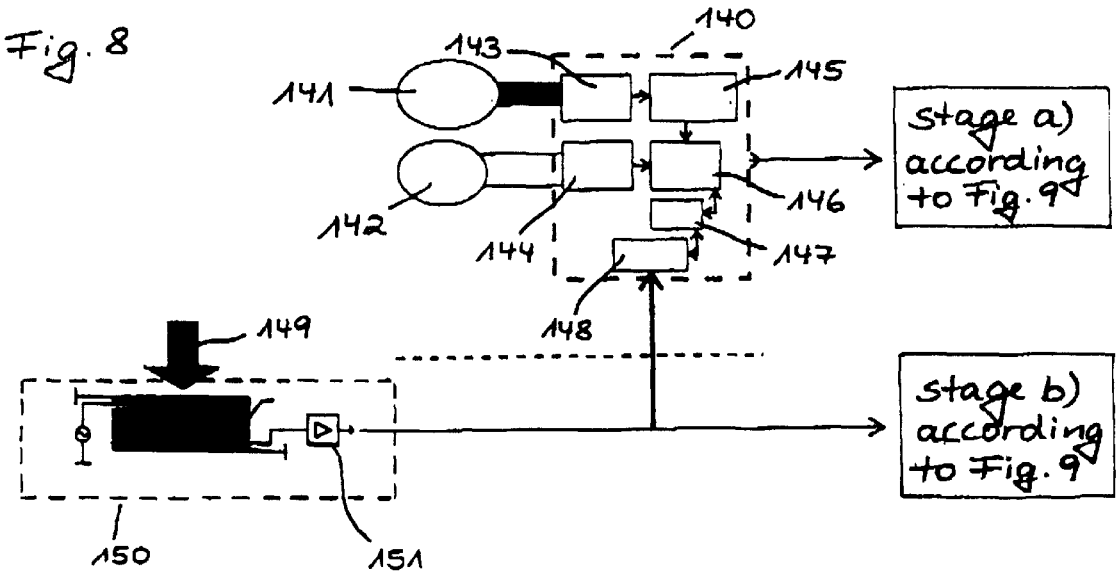

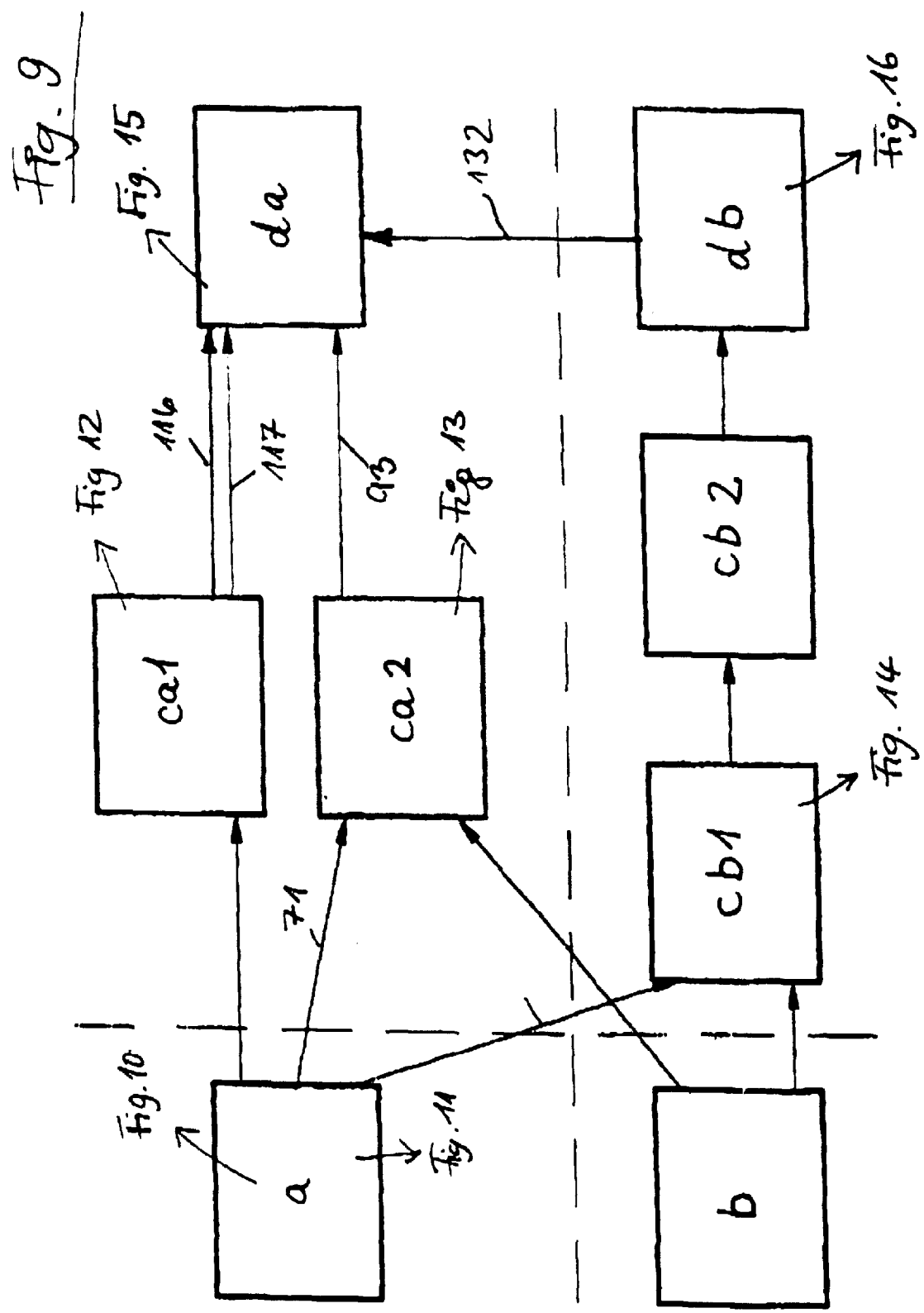

| beginning | end | action |
|---|---|---|
| 0 s | 2 s | standing upright |
| 2 s | 6 s | walking (5 Steps) |
| 6 s | 8 s | trunk bending |
| 8 s | 11.5 s | knee-bend |
| 11.5 s | 19 s | standing upright |
| 19 s | 23.5 s | taking load (10 kg) from the floor (leg lift) |
| 23.5 s | 26 s | standing upright with load weight |
| 26 s | 29 s | knee-bend (with 10 kg load) |
| 29 s | 30.5 s | standing upright with load weight |
| 30.5 s | 34 s | putting load on the floor (sideways) |
| 34 s | 36 s | standing upright |

METHOD AND DEVICE FOR THE RECORDING, PRESENTATION AND AUTOMATIC CLASSIFICATION OF BIOMECHANICAL LOAD VARIABLES MEASURED ON A FREELY MOVING TEST PERSON DURING A WORK SHIFT

BACKGROUND OF THE INVENTION

1. Field of the Invention

The invention relates to method and measuring system for the recording, presentation and automatic classification of biomechanical load variables measured on a freely moving test person during a work shift.

2. The Prior Art

Existing posture measuring systems only permit the determination of the movement and the position of individual parts of the body. U.S. Pat. No. 5,012,810, for example, determines movements of the spine without reference to a spatial coordinate system.

On the other hand, some systems for the prevention of job and work-related heath disorders and illnesses require connection to external memory and evaluation units and have a power supply (see Morlock et al., $2^{nd}$ Erfurt Conference, documentation of the $2^{nd}$ symposium of the Erfurt Conference of the $BGNG^2$, December 1995, published by: S. Radandt. R. Grieshaber, W. Schneider, monade Verlag und Agentur, Rainer Rodewald, Leipzig 1996, pages 215–238, ISBN 3-00-000673-7).

Measuring systems which work with markers on a body being examined and several cameras can usually only be used at specially equipped workplaces. Their area of application is therefore very limited (see Deurestzbacher, Rahder, "Ein CAE-basierter Zugang zur dynamischen Ganzkörpermodallierung—Die Kräfte in der lumbaien Wirbelsäule belm asymmetriachen Heben", Biomedizinische Technik 40, 1995, 93–98). Therefore this invention is an improvement over the prior art because it records the dynamic movements of an individual at an ordinary worksite.

SUMMARY OF THE INVENTION

The human spine is a double S-shaped, curved column of bone consisting of 33 to 34 vertebrae. It is divided into:

the concave (from front to back) cervical spine, the convex (from front to back) thoracic spine, the concave (from front to back) lumbar spine (5 lumbar vertebra, L1–L5), The sacrum (5 sacral vertebrae S1), the coccyx.

Since the lever arms of the abdominal and back muscles are very small in relation to the vertebral body or intervertebral discs (e.g. 5.5–7 cm for the extensors of the back), considerable muscular force is required to compensate for the resulting external torque. This in turn produces a high compression force on the discs. For example, the L5/S1 disc is subjected to a compression force of approx. 2.8 kN when a 75 kg man bands his upper body through 90° without handling a load weight. The bottom discs of the lumbar spine (L3/L4, L4/L5, L5/S1) are therefore, most prone to herniation.

Thus, the knowledge of posture and load weights handled is extremely important to assessing how dangerous an activity is for the spine.

To assess the biomechanical load on the musculoskeletal system, especially as a result of occupational activities, a method and a measuring system are required for the continual, automated recording of posture, body movements and load weights handled. This comprehensive system shall consist of sensors to determine the joint angles, the position of the spine, its torsion, and for measuring the ground reaction forces. It must be possible to store the signals measured by the aforementioned sensors and to present them in the form of biomechanical load variables.

A personal measuring system for recording the external load variables of occupational activities which involve the lifting and carrying of loads or which have to be performed in extreme postures must meet the following requirements:

Trunk and leg postures should be recorded with the aid of a robust system of sensors which is easy to attach. Ground reaction forces must be recorded by a portable measuring system, synchronous with posture angle determination.

The sensors should be attached to work clothing so that the system can be used as flexibly as possible at different workplaces. The sensors should not hinder the test person in his work.

The measuring system should be well-suited to practical application.

The entire measuring system (including energy supply and data memory) should be attached to the test person so that it is possible to dispense the external cable connections and so that measurements can also be recorded at workplaces with changing locations.

Data acquisition should take place with a sampling rate of at least 20 Hz. The memory of the portable data memory unit should be designed for a total measuring time of up to eight hours (one work shift).

To assess the measured data, there is provision for the automated identification of classified (e.g. according to OWAS) postures once measuring has been completed. A method must be developed which can be used to determine the load weights handled based on measured body angle data and ground reaction forces. The entire evaluation process should also be fully automated.

The invention was designed to collect the data necessary for assessing the load placed on the skeleton, especially the spine. The data collection should occur directly at the workplace without any measuring or power supply cables getting in the way and for the duration of one work shift. This data should be stored temporarily and evaluated automatically at the end of the shift. Using the data collected with the measuring system, dynamic processes should also be included in the load determination process for the human body to provide a complete picture of the nature and extent of the forces acting on a test person.

The invention makes it possible to determine joint angles based upon the position of the spine by using a system for the continual, automated recording of posture, body movement and loads handled together with sensors. The control unit for the cycled scanning of the idealized point of force application can determine and evaluate the loads on the spine.

Using the method described in this invention, it is possible to make statements concerning the external loads on the skeleton or part of the skeleton which occurs during individual work stages. This means that activities performed can be assessed according to kind, type and biomechanical load factor in keeping with occupational needs (e.g. prevention).

The invention allows the data recorded to be stored temporarily in the measuring system on the freely moving person. This means that data collection is not dependent on large-volume and heavy auxiliary equipment in the form of memories, computers and supply equipment. If required, data can also be evaluated directly at the workplace, as soon as measuring has been completed.

Various methods for analyzing and assessing work postures are known. The method with this invention is based on a data collection sheet for 84 basic work postures and three load weight classes and measures the frequency of movements of certain parts of the body in connection with load weights handled. The evaluation phase then establishes four empirically calculated load groups which result in an OWAS measures classification of each activity examined for the purpose of prevention. This method determines work postures which strain the body. Thus, this method prevents a harmful, excessive, or abnormal load from being placed on the supporting/locomotor system, e.g. by restructuring the workplace and/or modifying work organization.

Current data collection, posture and load weight identification methods are extremely time-consuming and labor-intensive, and only static postures are recorded. However, to assess work-related vertebral loads, information on body movement, load duration and velocity is particular important.

BRIEF DESCRIPTION OF THE DRAWINGS

Other objects and features of the present invention will become apparent from the following detailed description considered in connection with the accompanying drawings which discloses two embodiments of the present invention. It should be understood, however, that the drawing is designed for the purpose of illustration only and not as a definition of the limits of the invention.

In the drawings, wherein similar reference characters denote similar elements throughout the several views:

FIG. 7 is a flow diagram for comparing measured chronological and spatial motion sequences with standard values;

FIG. 8 is a block diagram of a circuit arrangement for recording and processing measured data;

FIG. 9 is an overview of the method for recording, presentation, automatic classification and assessment of biomechanical load variables;

DETAILED DESCRIPTION OF PREFERRED EMBODIMENTS

Figure 1:
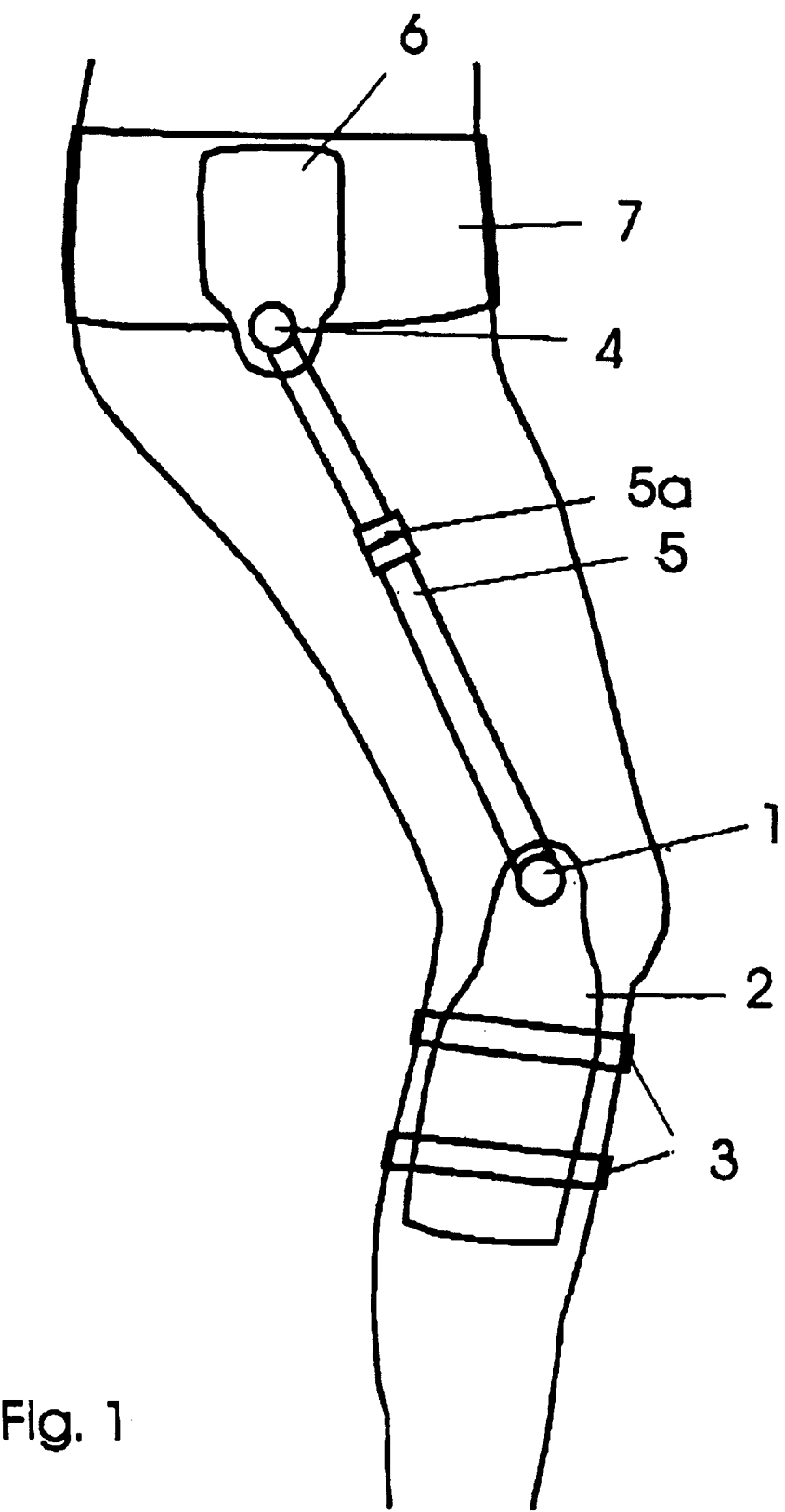
FIG. 1 shows a front view for the attachment of knee and hip angle sensors including an adjustable a connection which compensates for all compensating movements between a knee and hip joint.

Turning now in detail to the drawings, FIG. 1 shows the attachment of the knee and hip angle sensors. Sensors 1 for the knee angles are mounted on rails 2 which are adjusted to fit the lower leg and attached with Velcro® strips 3 to the lower leg over the clothing. Flexible, telescopic hip-knee connections, which can be adjusted to the length of the thigh and are easily detached at a quick-release catch 5a, are used to set both the knee angle sensors 1 and the hip angle sensors 4. The hip angle sensors 4 are fitted to molded plates 6 which are attached to the hip belt 7, which can be adjusted to fit the wearer's hips, by a Velcro® strip.

Therefore, no sensors are fitted on the thigh because there is a great risk that muscular movements will cause any sensors attached there to slip. The flexible, length-adjustable hip-knee connections 5 compensate for any compensating movements between knee and hip joint and the pivot point of sensor 1 remains exactly above the knee pivot.

Figure 2:
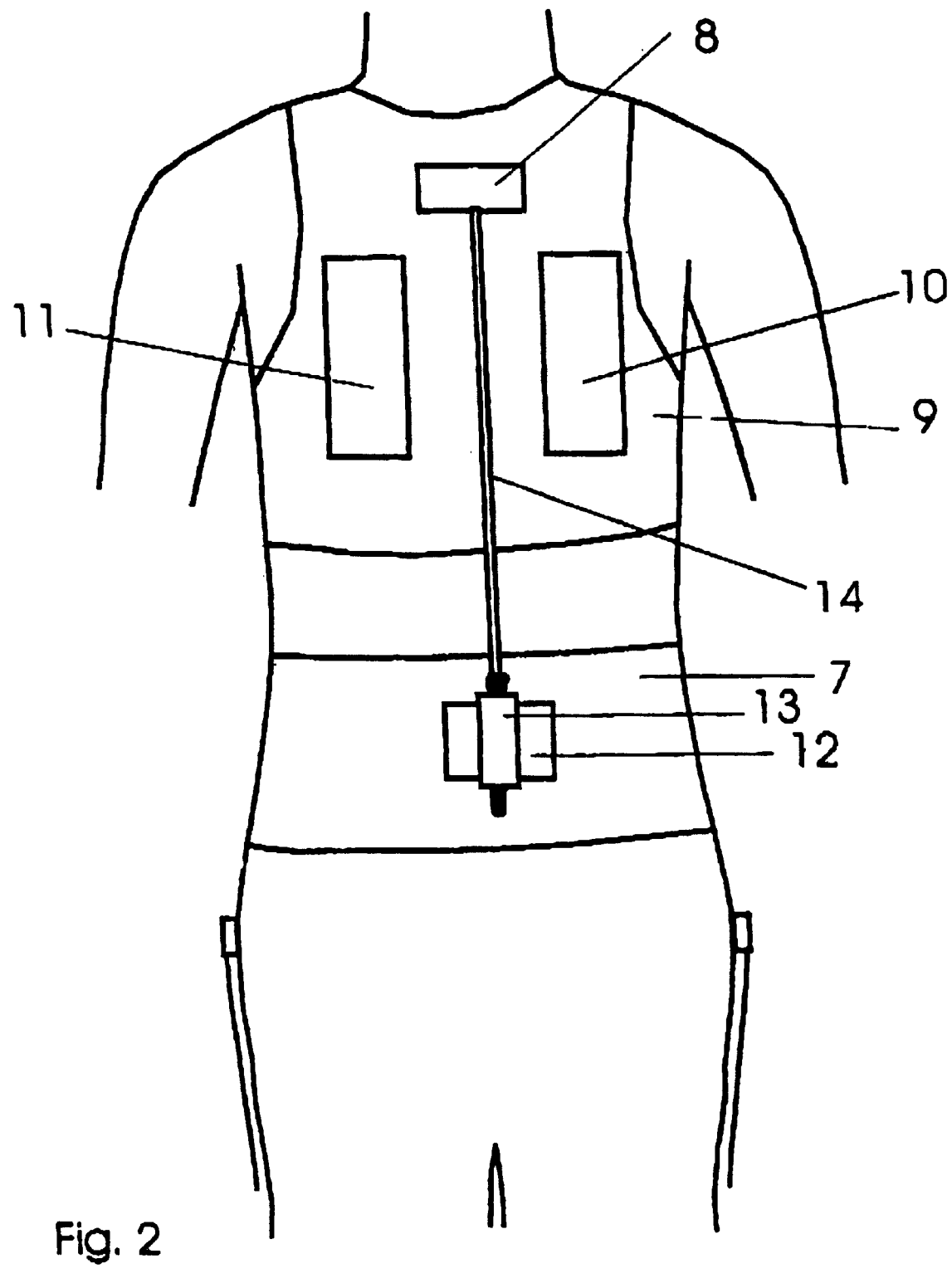
FIG. 2 shows a back view of the attachment of sensors for determining the position of the spine including a length-adjustment guide for the torsion actuator, controller and memory units, for the posture and ground reaction force measuring system.

FIG. 2 shows the attachment of the sensor unit 8, which records the sensors for flexion and lateral flexion in the region of the thoracic vertebrae and torsion of the spine, to a sturdy, breathable jacket 9. In addition, controller and memory units 10 and 11 for the posture measuring system and the ground reaction force measuring system are attached to jacket 9. Sensor unit 12 is attached to the hip belt 7. A torsion-proof guide 13 for the flexible actuator 14 of the torsion sensor is also attached to sensor unit 12. The flexible wave of torsion measuring unit 14 passes into a square metal bar 14a which is pushed into a guide 13 where it remains movable in a vertical direction. Torsion meter guide 13 is connected to the sensor box 12 via a hinged joint 13a.

Lower sensor box 12 contains the sensors for measuring trunk flexion (lumbar spine region) and connections for the leg angle potentiometers.

Sensor unit 8 contains two inclinometers with consecutive measuring ranges so that an angular range of more than 180° can be covered. The data measured by the sensors are read out at a sampling rate of 20–50 Hz so that dynamic processes can also be recorded. They are stored on an easily exchangeable memory with sufficient capacity for storing all the data from one work shift (e.g. flash cards).

Sensors for determining the inclination of lumbar and thoracic spine consist of one gyroscope and two inclinometers whose signals are stored separately and combined during evaluation. Additional measuring instruments such as potentiometers, goniometers, etc. can be attached to determine the position of other joints, e.g. arms.

Figure 3:
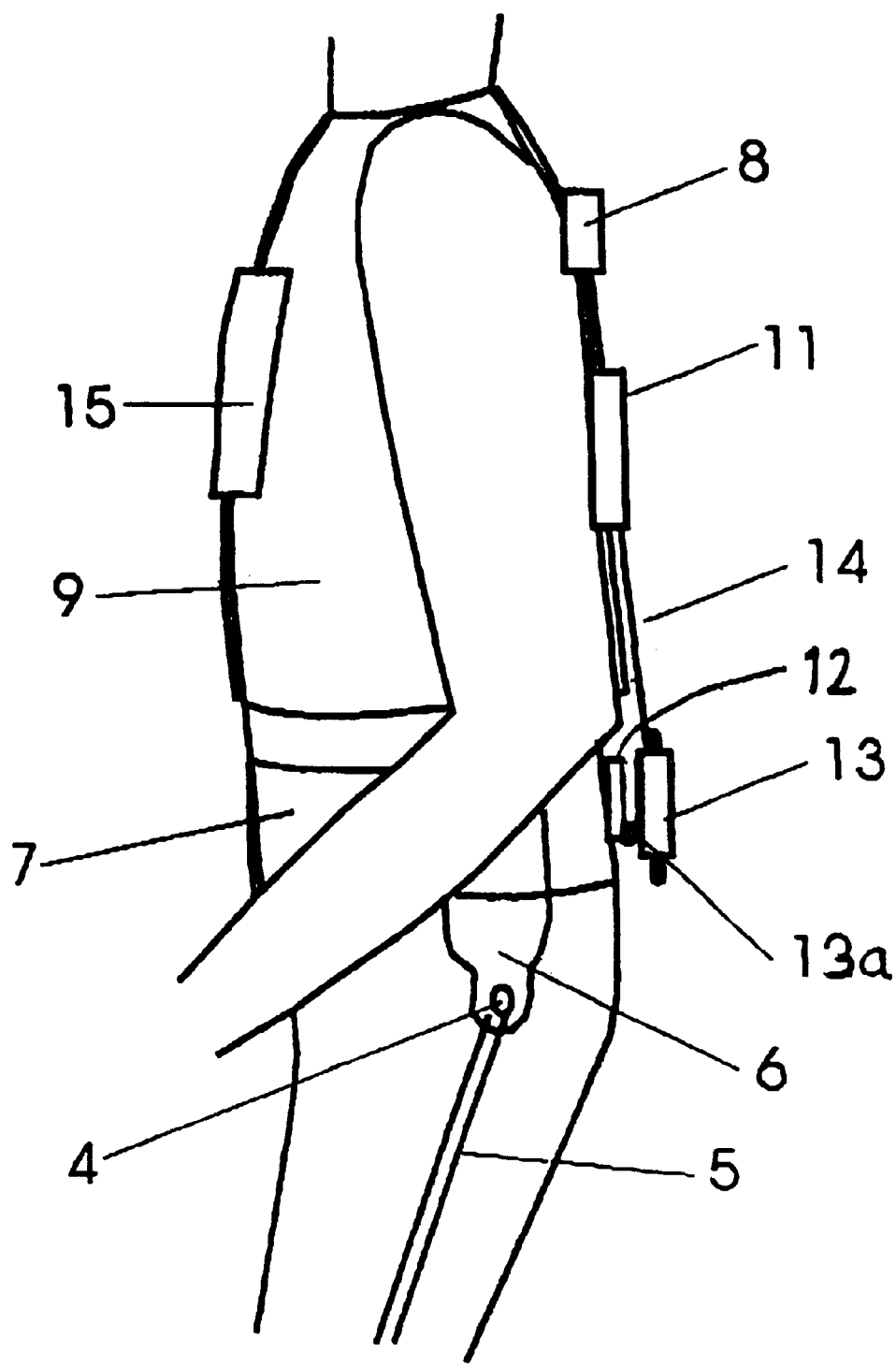
FIG. 3 shows a side view of the attachment of the energy supply sources.

FIG. 3 shows the attachment of energy supply source(s) 15 to jacket 9 and the attachment of sensor units 8 and 12 and controller unit 11 from the side. According to the invention, the parts of the measuring system can be fitted to the test person's chest and back so that there is an even distribution of weight.

This leaves the attachment of a microcontroller for measuring ground reaction forces and an evaluation unit in which the measured data is converted into absolute spatial co-ordinates and assigned to posture classes.

Figure 4:
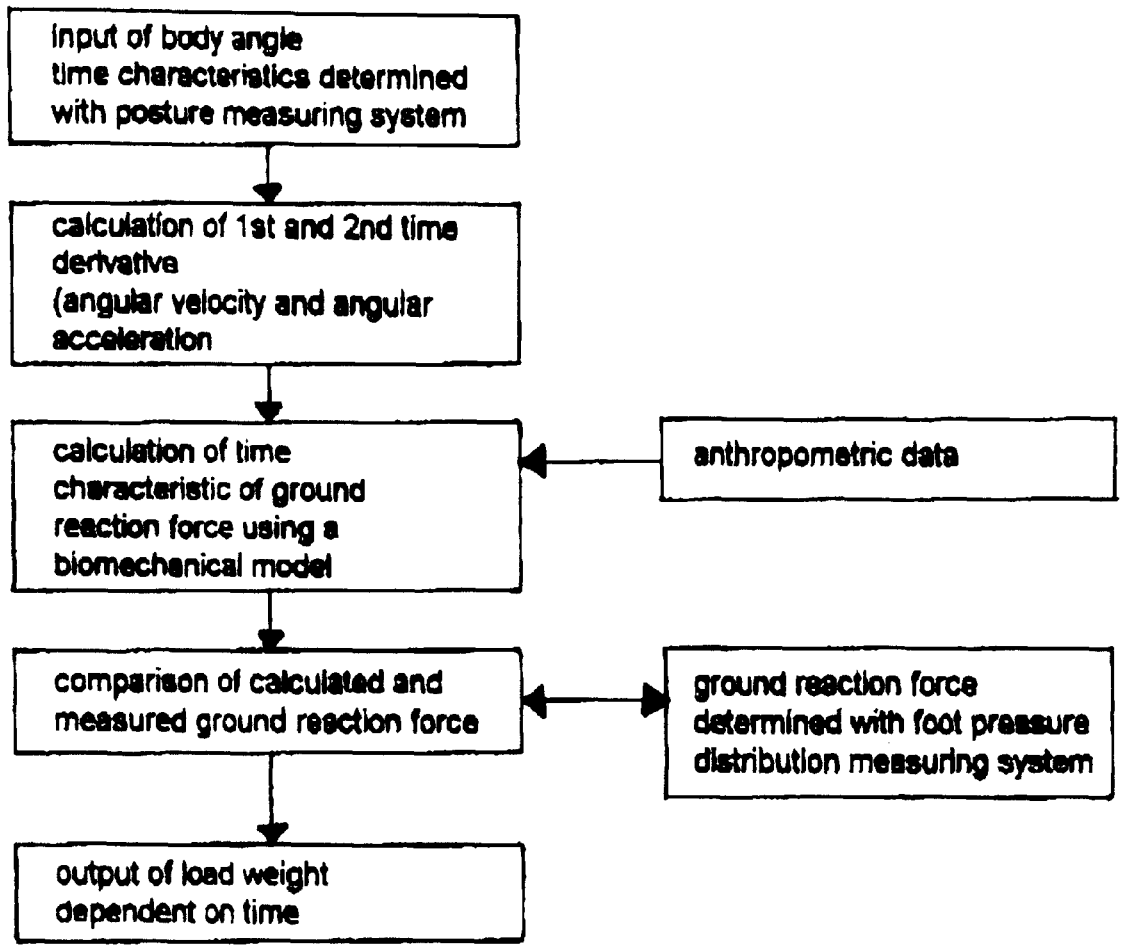
FIG. 4 is a flow diagram for determining externally exerted forces (load weights)

The method for determining the load picked up or the externally exerted forces is presented as a flow diagram in FIG. 4. The invention measures the angular velocity and angular acceleration for each sampling cycle based on the angles measured. The ground reaction force is calculated on this basis, taking anthropometric data into account. Finally, the load picked up is determined by comparing the ground reaction force measured by the foot pressure distribution measuring system with the ground reaction force calculated based on the body angles.

Figure 5:
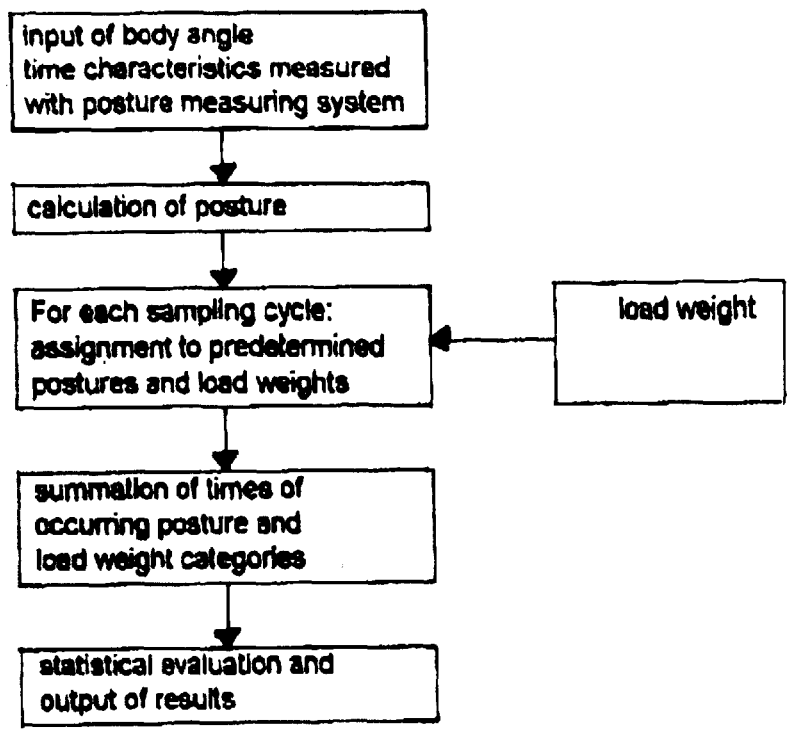
FIG. 5 is a flow diagram for assigning measured postures and load weights to predetermined postures and weights.

FIG. 5 provides a schematic representation of the method for assigning measured postures and load weights to predetermined values and their further processing. In a further stage, the results obtained can be extended to include medical assessments, which are statements concerning necessary changes to the activities examined.

Figure 6:
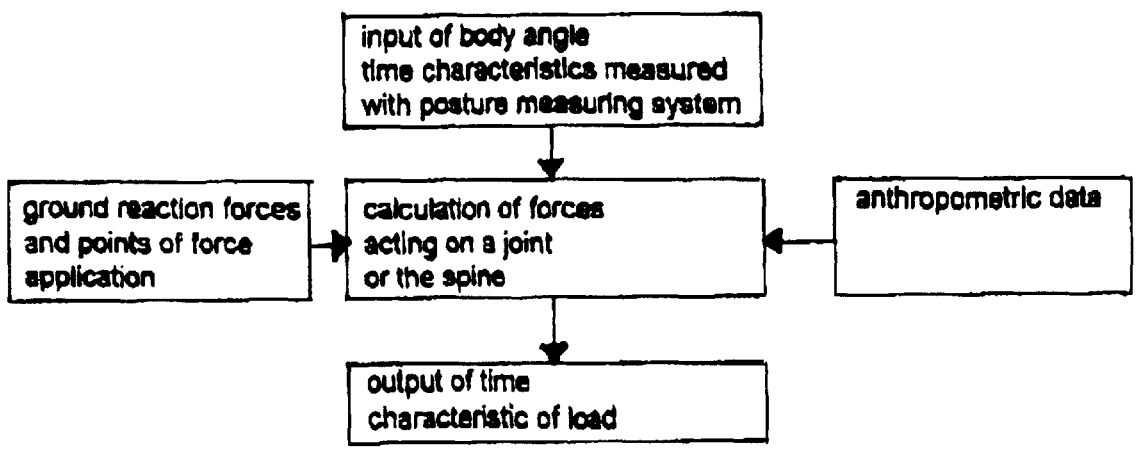
FIG. 6 is a flow diagram for determining the load on a joint or a point of the spine with the aid of a dynamic model of the body.

FIG. 6 shows the flow diagram for calculating the load on a joint or the spine based on the measured time characteristics for body angles (angular velocity, angular acceleration), the measured ground reaction forces, idealized points of force application and anthropometric data (height, weight, position of centers of gravity).

Total force due to weight is reconstructed on the basis of ground reaction force (measurement) and ground reaction force (model prediction) characteristics. Ground reaction force can be determined from the pressure distribution of the right/left measuring soles. To determine force due to weight (body and load weight) and its distribution over the soles of the feet, a commercial foot pressure distribution measuring system with a portable microcomputer and memory unit 11 is used which controls the synchronous sampling of the body angles via a synchronizing pulse with the measuring system described above. The data stored is evaluated automatically as described below, once measuring has been completed.

To calculate the expected total ground reaction force, the acceleration and velocity components are calculated from the derivatives of the measured body angles and the calculated values transformed into individual joint forces and individual joint moments.

The flow diagram in FIG. 7 illustrates a further way in which the measured values can be used, by comparing standard values with the body angles determined and the angular velocities and accelerations calculated, from which it may be possible to conclude any functional limitations.

The following describes the automated recording of vertebral loads based on the example of an occupational activity. An overview of the method for the recording, presentation and automatic classification of biomechanical load variables can be seen in FIG. 9.

The time characteristic of body angles is measured in stage a of FIG. 9. Details are explained in the following diagrams 10 and 11.

Parallel to this, the ground reaction force and the points of force application in the sole region are measured in stage b.

The results of measurements in stages a and b are utilized firstly, following ergonomic assessment (stages ca1 and ca2), as a load profile of the occupational activity (stage da) and secondly, following biomechanical evaluation in stages cb1 and cb, to present the time characteristic of the disc compression force (stage db). Further block diagrams were created for the ergonomic assessment (FIG. 12, FIG. 13) and biomechanical evaluation (FIG. 14).

Figure 10:
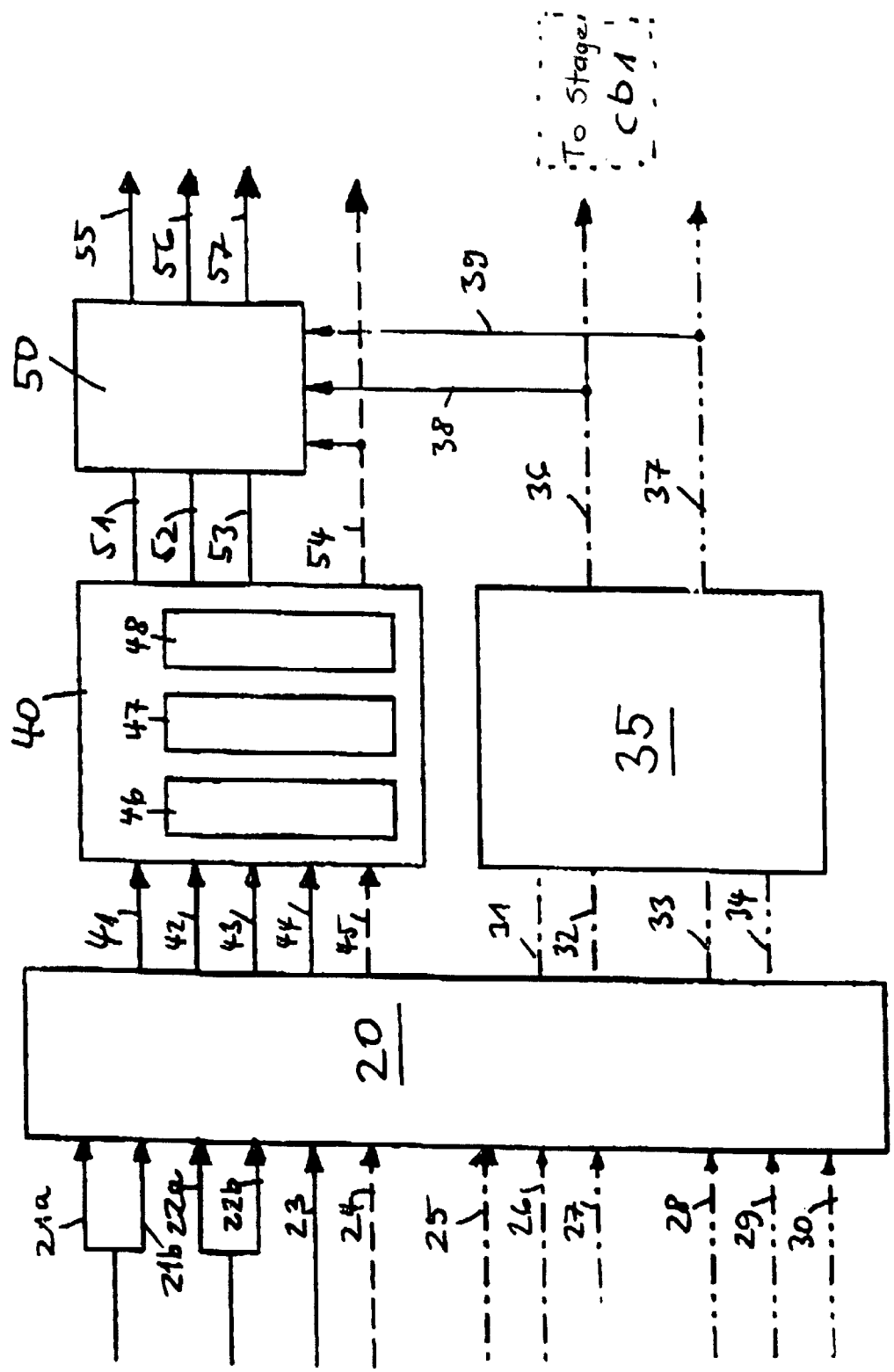
FIG. 10 is a schematic representation of signal conditioning.

Signal conditioning in stage a is presented in the diagram in FIG. 10. The following signals are input as electrical measured values into a calibration stage 20 which consists of multipliers, adders and memory units: left and right knee angle signal 21a, 21b, left and right hip angle signal 22a, 22b, leg torsion signal, leg lateral flexion signal 22, 23. The signals 21–23 represented by the continuous line were measured with a potentiometer and are therefore relative values; the signals 24–30 represented by the dotted line were measured with gyroscopes or inclinometers and therefore constitute absolute angle signals as explained further below. After passing through the calibration stage 20, these absolute signals are input via signal lines 31–34 into a signal mixing unit 35 comprising integrators, adders and multipliers. Following the numerical integration of the gyroscope signal for trunk flexion (signal 25), the corresponding inclinometer signals 26, 27 are admixed during each sampling period. The procedure is the same for the trunk flexion angle and for the thoracic spine. Following numerical integration, the gyroscope signal 28 is continually added to the inclinometer signal 29, 30 during each sampling period. This produces two stabilized signals, thoracic spine (TS) flexion angle signal 36 and lumbar spine (LS) flexion angle signal 37.

These signals 36 and 37 are either input directly into stage cb1 for calculating individual joint forces and individual joint moments, or they are used as signals 38, 39 to convert the relative body angle measurements into absolute angle information 21–23.

In addition, interference and noise is removed from the signals 41, 42, 43, 44, 45 taken from the calibration stage 20 in filter unit 40. This is achieved with the aid of usual electronic components, consisting of fast Fourier transform 46, multiplication with low-pass filter function 47 and inverse transformation 48.

Following this procedure, the filtered signals 51, 52, 53, 54 enter the conversion unit 50 where the relative angle signals are converted into absolute spatial angle signals 55, 56, 57 related to a vertical axis. The results can then be examined in stage ca1 to identify motion patterns.

Figure 11:
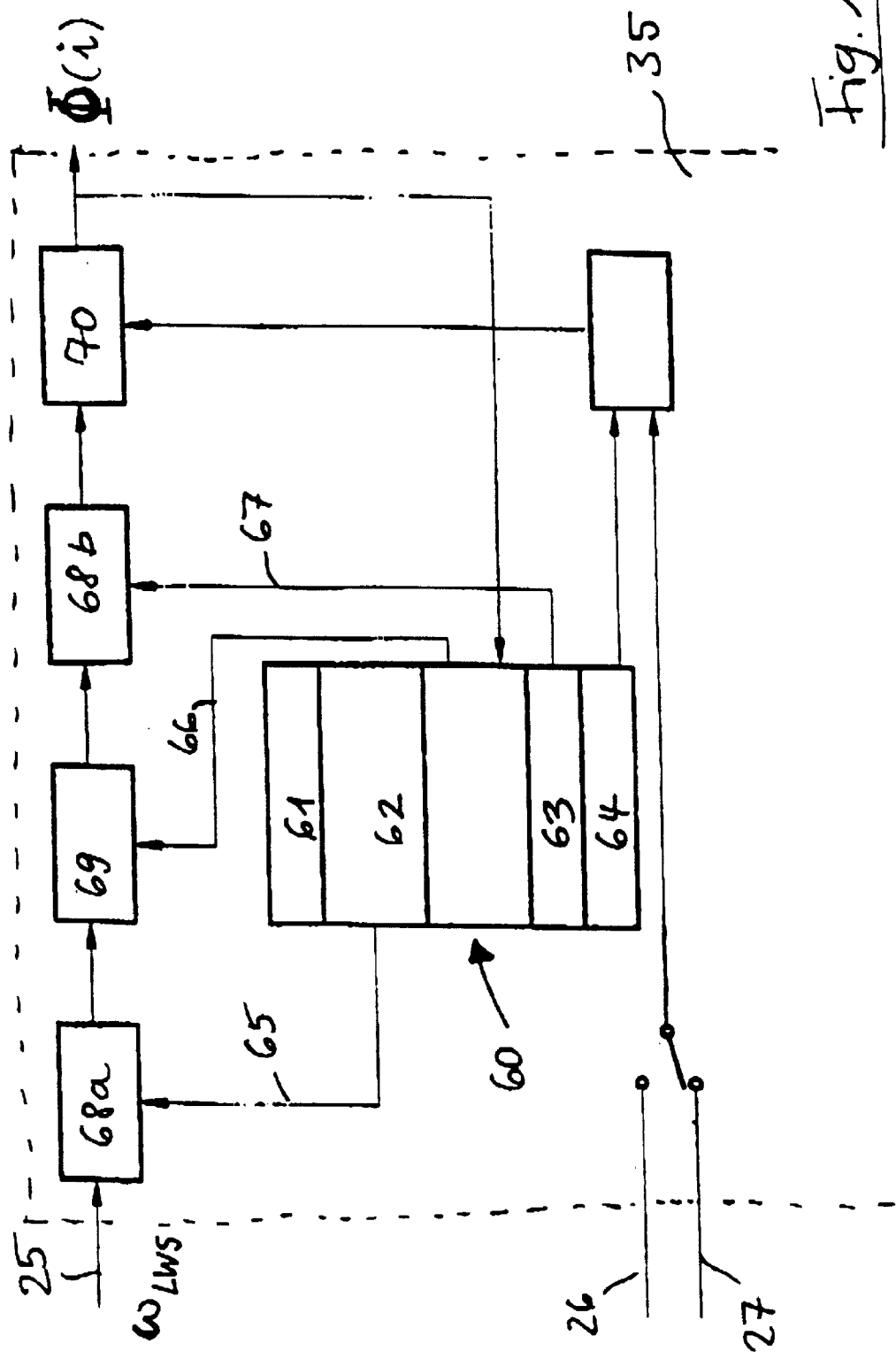
FIG. 11 is a schematic representation of the operating principle of the signal mixer.

FIG. 11 provides a schematic representation of the operating principle of the signal mixer 35. Gyroscope signal 25, $\omega_{gyro}$ which indicates a trunk flexion (lumbar spine), serves as an input signal. Inclinometer signals $\Phi_{INCL}$ 26, 27 are marked on the partial section of signal mixer 35 as further input signals. Signal 26 represents the inclinometer range of lumbar spine in the spatial range 0–120° and signal 27 represents the inclinometer range of the lumbar spine from 120–140°. Signals 28, 29, and 30 are mixed with gyroscope signal 25 in the same way for the thoracic spine.

The most important element of the signal mixer 35 is the central unit 60, which comprises a memory 61, a sampling interval unit with the sampling frequency $1_{80}$ and the mixing factor units $K_1$ for the gyroscope signals 63 and $K_2$ for the inclinometer signal 64. $K_1+K_2=1$. Preferred values are $K_1=0.9$ and $K_2=0.1$.

Signal mixing takes place in the central unit 60 according to the function $$\Phi(1)=(\Phi(1-1)+\omega_{gyro}(1)\cdot(f_A)^{-1}\cdot K_1+\Phi_{INCL}(1)\cdot K_2$$

with signal lines 65, 66, 67 directed to the multipliers 68a, 68b and adder 69. The continual addition of the inclinometer signals 26 and 27 via the adder memory unit 70 produces a stabilized angle signal φ which is used for both ergonomic assessment in stages ca1, ca2 and for the biomechanical evaluation in stages cb1, cb2. It is only possible to make statement regarding motion patterns, externally exerted forces and the expected total ground reaction force if measured body angles with spatial reference (in this case, related to the vertical spatial axis) exist.

According to FIG. 9, threshold values for identifying motion patters are formed in stage ca1 and the externally exerted forces determined in stage ca2. Stage ca2 receives the following body angles with spatial reference via line 71 (cf. FIG. 13): trunk torsion line 72; trunk lateral flexion line 73; trunk flexion LS line 74; trunk flexion TS line 75; hip angle left/right line 76; knee angle left/right line 77.

Figure 13:
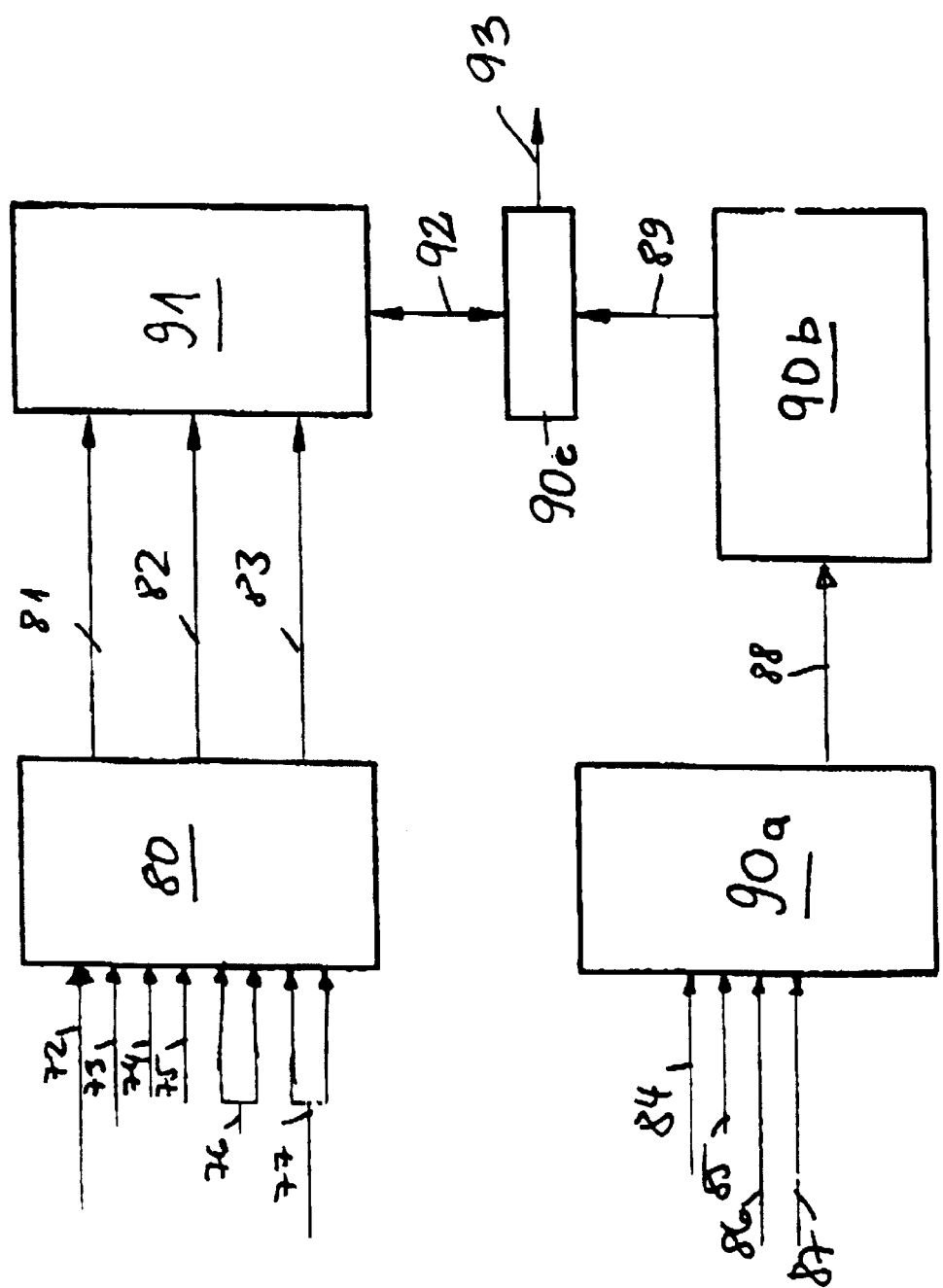
FIG. 13 is a schematic representation of the predicted total ground reaction force based on the body angles.
Figure 14:
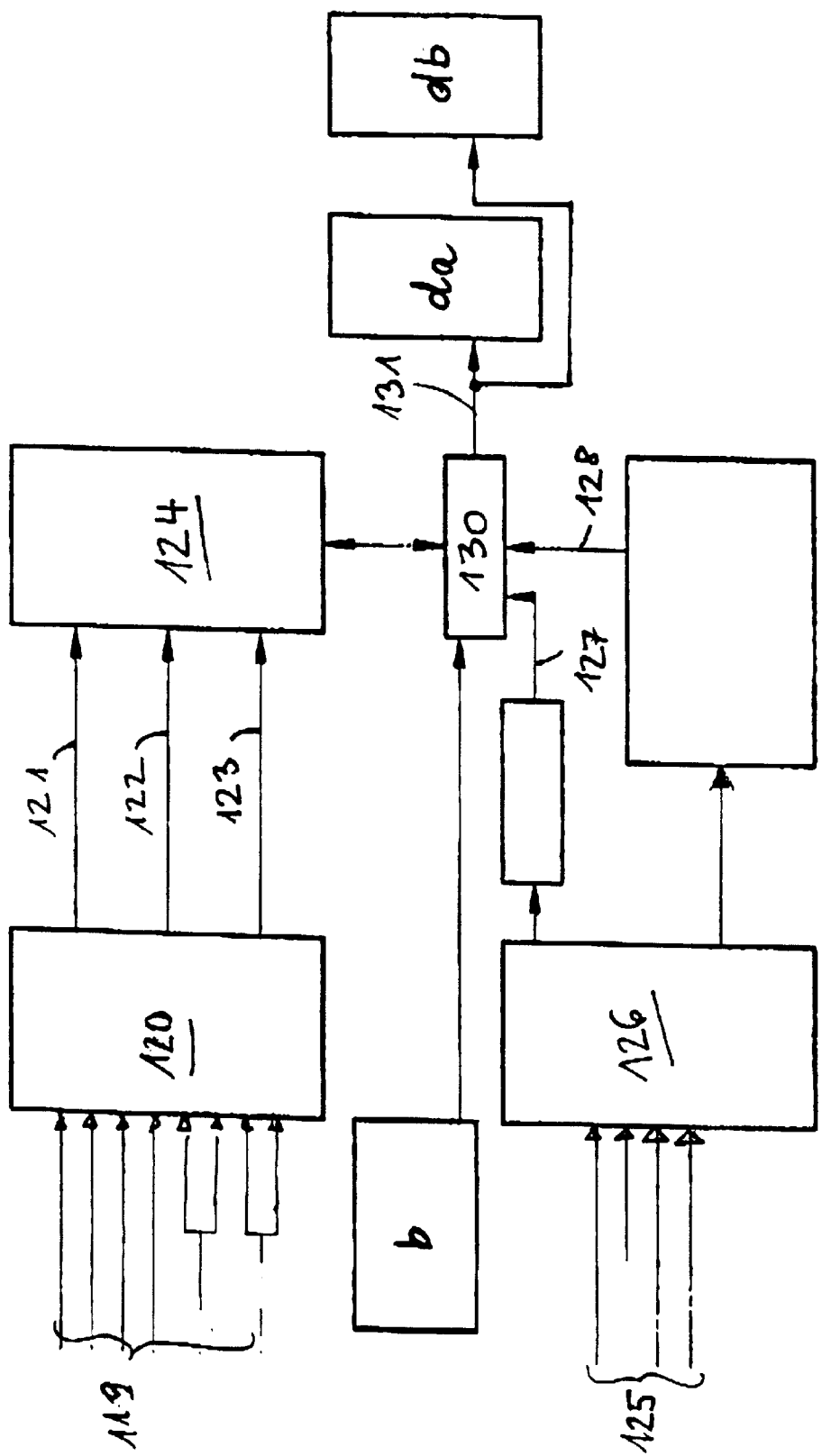
FIG. 14 is a schematic representation for determining compression force, e.g. in the lumbar spine region.

According to FIG. 13, differentiation 80 summarizes these body angles into three signal units 81, 82, 83 for the trunk region, the hip region, and the knee region, with angular velocities and angular acceleration values also determined for the respective angles. The data from an anthropometric data memory 91a, contains the dimensions of the test person, such as height 84, weight 85, sex 86, and age 87. The anthropometric database 90b which contains standard body data, such as weight and dimension of parts of the body, position of the centers of gravity of parts of the body and type of joints are read into memory 90c via line 88 and 89 respectively. An exchange with measured data register 91 via line 92 makes it possible to determine the expected total ground reaction force without taking account of externally exerted forces. This total ground reaction force $F_{mod}$ can be retrieved via line 93.

Figure 12:
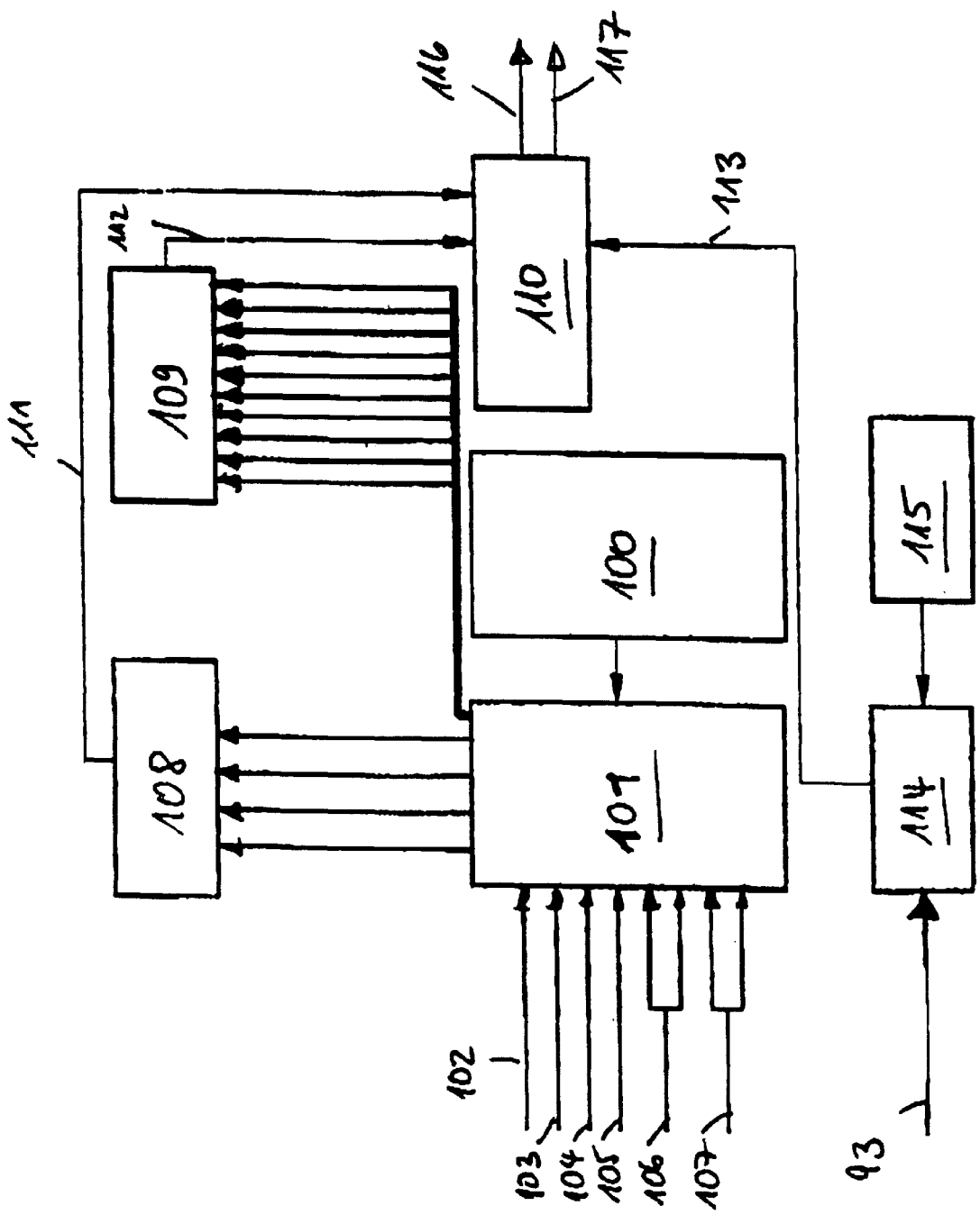
FIG. 12 is a schematic representation of the principle for determining threshold values and for the output of the load profile in the form of motion patters and externally exerted forces.

FIG. 12 shows how threshold values are determined according to stage ca1 and the output of the load profile in the form of motion patterns and externally exerted forces. A memory 100 which contains the body angle threshold values for the clear characterization of postures can be considered the central unit here. The memory 100 is connected to a comparator 101 into which the body angle signals with spatial reference, such as trunk torsion 102. Trunk lateral flexion 103, trunk flexion LS 104, trunk flexion TS 105, hip angle left/right 106, knee angle left/right 107, are also fed. The comparator 101 is then connected to a memory 108 for the back posture numerical code and a memory 109 for the leg posture numerical code. Both memories are connected via lines 111, 112 to the limit comparator 110 into which a line 113 leads from the comparator 114. The comparator 114 compares the total ground reaction force from lien 93 with the load weight classes contained in memory 115. In this way, load profiles in the form of motion patters and externally exerted forces can be called up in the limit comparator 110 via lines 116, 117.

To determine individual joint forces and moments and the disc compression force in stages cb1 and cb2, the measured body angles must be converted into body angles with spatial reference in accordance with stage a in FIG. 9 or FIGS. 10 and 11. These are described in FIG. 14 as signal group 119. Once the corresponding angular velocities and angular accelerations have been determined in differentiator 120, the results are passed onto the multiplier 124 via signal lines 121, 122, 123.

Parallel to this, following the input of the test person's body data via signal group 125, the values for the functional muscle anatomy are input via line 127. In addition, the values for the dimensions, weights of parts of the body, position of centers of gravity of parts of the body and type of joints via line 128 are also input into the central memory 130 with the aid of an anthropometric database 126. Data is exchanged via line 129, with joint forces, joint moments and disc compression forces being passed onto the process stages da, db via line 131.

Figure 15:
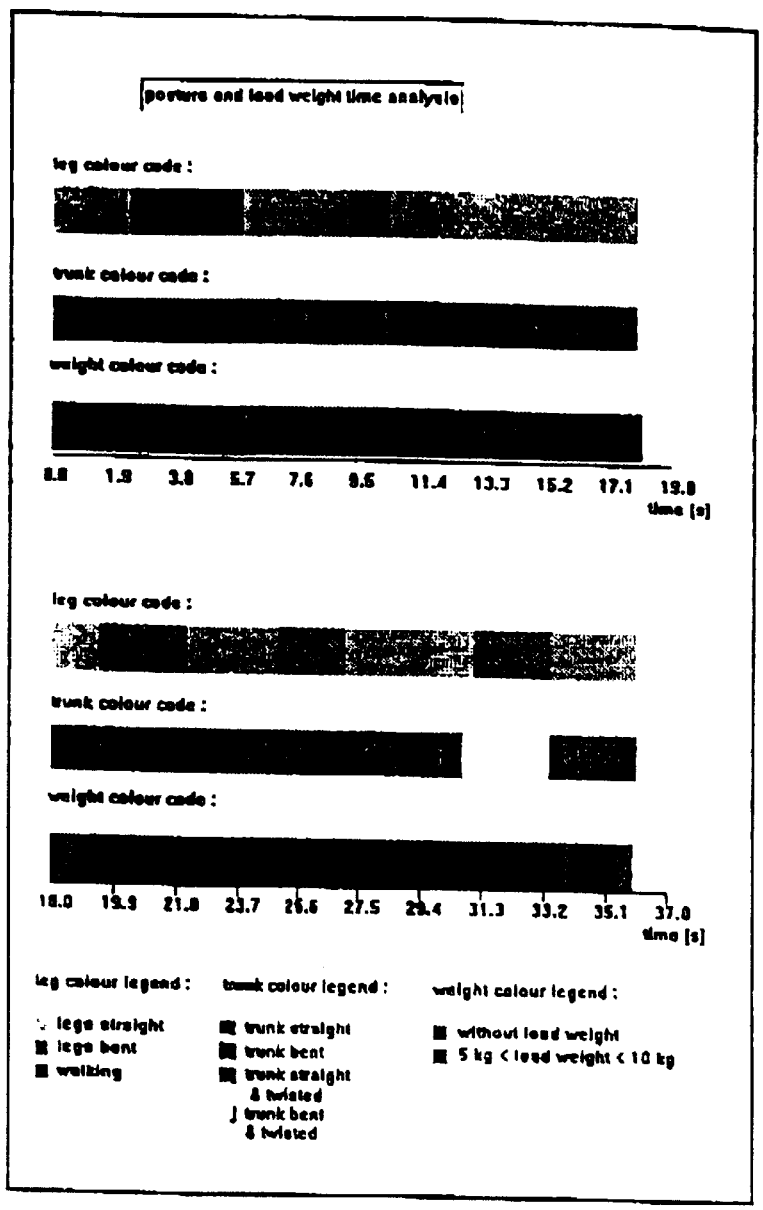
FIG. 15 is sample extract from a load profile (corresponding to da in accordance with FIG. 9). The sequence of motions took place in accordance with an OWAS color bar representation with corresponding interpretation.
Figure 16:
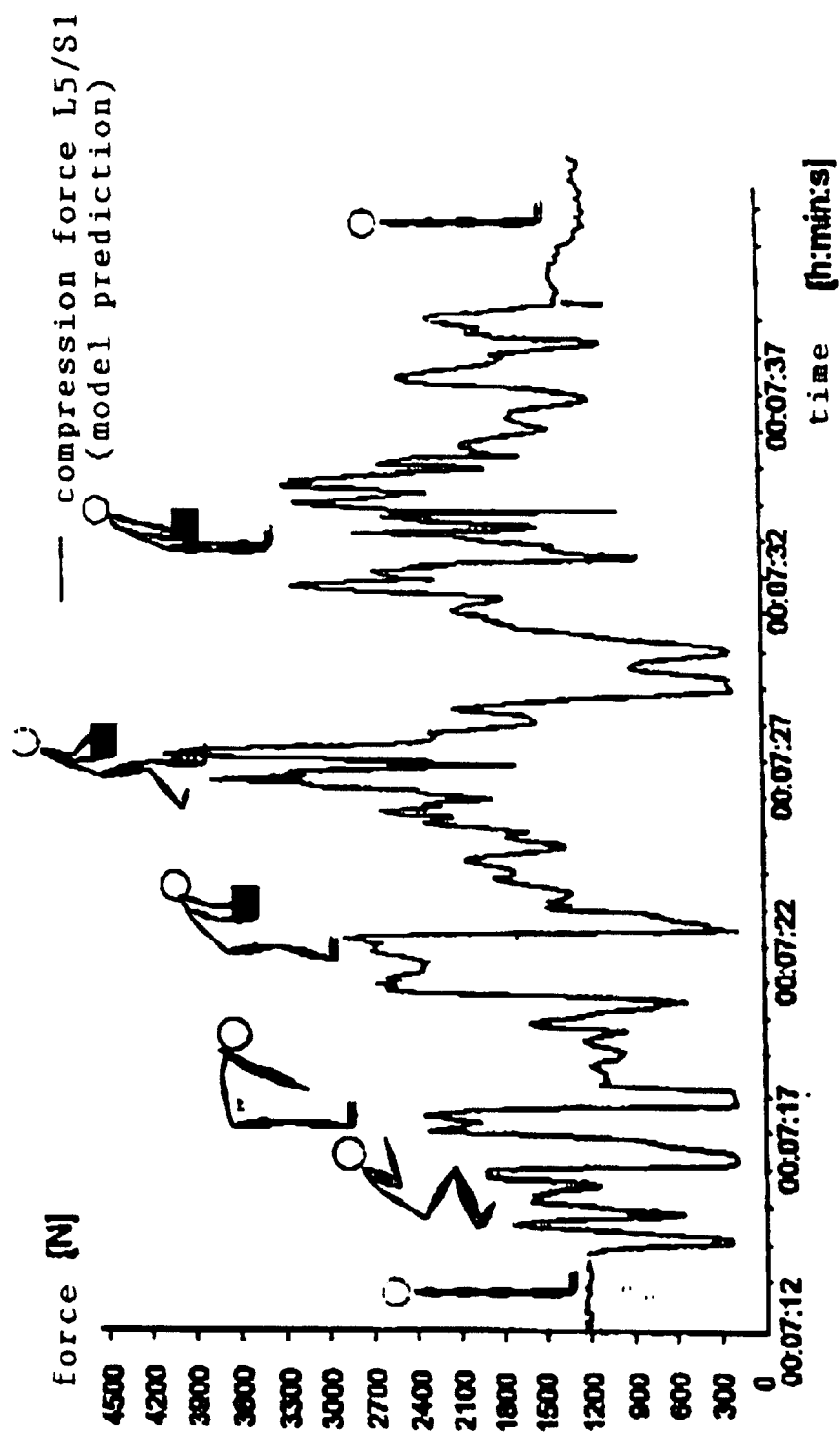
FIG. 16 is an example of the time characteristic of predicted L5/S1 disc compression forces (corresponding to db in accordance with FIG. 9) and a representation of the assessment procedure in the form of a "vector man".

The results of the process stages da and db are presented by way of example in FIG. 15 and FIG. 16.

FIG. 15 shows an extract from a sequence of movements using the OWAS color bar representation and corresponding interpretation. The activity sequence can be seen from time t=0 s in the following order: standing upright, picking up a load weight (12 kg) with the trunk and knees bent, holding the load, bending the knees with the load, holding the load, putting down the load with the trunk bent and twisted and the knees bent, standing upright. The signals 116, 117 are 93 are fed into the process stage da. Signal 116 contains an angle value corresponding to the applicable OWAS code. Signal 117 indicates the respective load peaks, signal 93 indicates the expected total ground reaction force $F_{mod}$ as a characteristic quantity, without taking account of the externally exerted forces.

The result of the process stage db is a representation of the time characteristic of the disc compression force as a load indicator for stacking heavy boxes. This can be presented, for example, in the form of FIG. 16 as a prediction of the LS/S1 disc compression forces. Feedback is also possible to the process stage da, via line 132 which means that an overall assessment can be displayed in a single diagram. In this case it is particularly useful to supplement the visual representation with the "vector man" which makes it possible to verify the measured posture data in real time on the screen or the load profile printout. FIG. 15 includes code designations and FIG. 16 a "vector man" representation.

Accordingly, while one embodiment of the present invention have been shown and described, it is to be understood that many changes and modifications may be made thereunto without departing from the spirit and scope of the invention as defined in the appended claims.

What is claimed is:

1. A method for the recording, presentation and automatic classification of biomechanical load variables for classified postures measured on a freely moving test personal during a work shift, comprising the steps of:

(a) measuring a set of body angles over a period of time, on the freely moving test person during physical activity;

(b) measuring a ground reaction force and the points of force application in a region of a sole of a foot of the test person;

(c) determining threshold values for the identification of postures and comparing of the threshold values determined with the measured body angles to identify a set of motion patterns;

(d) calculating an expected total ground reaction force based on the measured body angles together with a set of corresponding anthropometric data;

(e) subtracting the measured total ground reaction force from the expected total ground reaction force to determine a set of externally exerted forces;

(f) identifying the motion patterns and an output of load profiles;

(g) deriving the acceleration and velocity component of the measured body angles and transforming them into individual joint forces and joint moments while taking account of the measured ground reaction force;

(h) deriving a disc comparison force; and (i) presenting the time characteristic of the disk compression force as a load indication, so that a set of test numbers is derived for use in the study of load variables on individuals in a work site.

2. The method according to claim 1, wherein the step of measuring the ground reaction force is performed capacitively and the measuring signal is passed on via an amplifier operating on AC voltage to an analog-to-digital converter.

3. The method according to claim 2, wherein the ground reaction force is determined based on the pressure distribution in a measuring sole.

4. The method according to claim 3, wherein the step of calculating the expected total ground reaction force involves determining the individual joint forces by adding up the individual weights and the measured kinematics of the corresponding body parts, and their vertical components.

5. The method according to claim 1, wherein the data measured on the test person is stored temporarily and, at the same time, pre-processed within a time interval which extends up to the end of the measuring period for evaluation.

6. The method according to claim 1, wherein the measured data in this output is presented in the form of a "vector man" representing a sequence of motions.

7. The method according to claim 6, wherein measurements are calibrated by comparing the posture of the test personal with the "vector man" at the start and the end of a measuring series.

8. The method according to claim 1, wherein the step of driving the disc compression force in the region of the lumbar vertebrae includes the steps of determining individual joint forces by taking account a set of relevant lever arms, and determining the moment of equilibrium around the center of gravity of the intervertebral disc.

9. The method according to claim 1, wherein the step of determining the body angles related to the vertical axis includes determining the area formed from a combined signal of the inclination velocities measured by gyroscopes and the inclination angles measured by inclinometers, to form the large flexion angles in the regions of the thoracic and lumbar vertebrae.

10. The method according to claim 1, wherein the body angles are measured and related to the vertical axis angle and velocity signals are measured with a sampling rate of 10–100 Hz.

11. The method according to claim 1, wherein the step of determining the body angles are determined using measurements from an instrument selected from the group consisting of a relative potentiometer, goniometer, and inclinometer.

12. The method according to claim 9, wherein the large flexion angle is stabilized using a combined signal produced by adding the numerically integrated gyroscope signal to the inclinometer signal during each sample.

13. The method according to claim 9, wherein the step of identifying motion patterns includes the steps of:
   determining a set of individual values, measured by the gyroscope, and inclinometer sensors and the potentiometers and converted to the vertical axis; and
   subtracting said individual values from said threshold values.

14. The method according to claim 1, further comprising the step of transforming measured body angles into motive forces by determining the velocities and acceleration based on the mathematical derivatives of the measured angles and calculating the joint forces and the joint moments acting on the center of gravity, taking account of the joint type, the respective position of the center of gravity and the forces due to the weight of the parts of the body concerned.

15. The method according to claim 1, wherein the expected total ground reaction force is determined based on the measured body angles of angular velocity, and angular acceleration and the anthropometry which is the size, weight, position of centers of gravity of the parts of the body.

16. The method according to claim 1, further comprising the step of determining load peaks based on the measured forces due to weight and compared with a peak dose which is the force-time-load.

17. The method according to claim 1, wherein the threshold values are defined as positive and negative angle variables and wherein a signal is triggered to identify a movement when the variables are exceeded or undercut.

18. A measuring system for recording biomechanical load variables for posture and body movement comprising:
   a series of angle sensors attached to a test person's joints and spine for measuring and recording a person's posture and body movement; and
   a series of measuring and storage electronics having a series of sensor combinations, wherein said sensor combinations each comprise at least two inclinometers covering an angular range of at least 180 degrees and at least one gyroscope to measure the position of the spine in relation to a fixed vertical axis of at least two points; and
   an evaluation unit for weighting a series of output signals said evaluation unit received from said at least two inclinometers and said at least one gyroscope wherein said evaluation unit calculates said output signals as a single value.

19. The measuring system according to claim 18, further comprising a foot pressure distribution measuring system for recording a ground reaction force with a same sampling rate as a set of posture equipment;
   wherein said series of angle sensors include knee angle sensors, mounted on a set of rails and adapted to be attached to a test person's lower leg over an article of clothing and adjusted in relation to a position of a knee joint;
   wherein said series of angle sensors include hip angle sensors that are preferably a series of potentiometers, and are mounted on a series of molded plates and are adapted to be attached to an adjustable hip belt worn over a test person's clothing and which can be adjusted as required in relation to the position of a test person's hip joints wherein there is at least one hip angle sensor and at least one knee angle sensor each disposed on one side of the system, and said angle sensors being set in accordance with the test person's posture by a flexible detachable connection having a quick-release catch;
   wherein said system further comprises:
   a set of sensor combinations disposed on the hip belt for measuring a flexion in a test person's lumbar spine wherein said set of sensor combinations are attached in a sagittal plane relative to a vertical axis wherein said set of sensor combinations are adapted to be attached to a jacket worn over the clothing to measure a flexion of a thoracic spine in said sagittal plane relative to said vertical axis;
   an inclinometer for measuring the flexion of the thoracic spine in the lateral plane relative to the vertical axis, and adapted to be attached to said jacket in a region of a test person's thoracic vertebrae; and
   a potentiometer for measuring a twisting of the spine between the regions of said lumbar vertebrae and said thoracic vertebrae wherein said potentiometer is adapted to be attached to said jacket in the region of said thoracic vertebrae, and set via a torsion-free connection to a guide attached to the hip belt in the region of the lumbar vertebrae which is used to adapt to changes in length.

20. The measuring system according to claim 18, further comprising:

- a set of equipment for a synchronous sampling of said series of angle sensors and said foot pressure distribution measuring system wherein said equipment for synchronous sampling comprises an energy supply source, a microcomputer unit for activating and scanning the sensors and a memory unit wherein said equipment is attached to said jacket;
- a set of equipment for determining a load handled based on a posture and a ground reaction force data registered by the measuring system wherein said equipment for determining the load handled consists of a control system for receiving said registered posture and said set of ground reaction forces as an input signal and the calculated ground reaction forces as a reference variable;
- a set of equipment for a continual comparison of a determined posture and a load weight data and their assignment to a set of predetermined postures and load weights and their weighting;
- a set of equipment for determining a set of forces acting on certain parts of the skeleton, especially the spine, and for determining a time characteristic based on the determined posture and load weight data using a dynamic model of the human body; and
- a set of equipment for comparing the determined chronological and spatial motion patterns of joints or the spine with specified standard values to establish functional limitations.

* * * * *